US012734203B2

(12) United States Patent
He

(10) Patent No.: US 12,734,203 B2
(45) Date of Patent: Sep. 15, 2026

(54) MULTIVITAMIN FOR ADJUVANT TREATMENT OF TUMOR, AND PREPARATION METHOD AND APPLICATION THEREOF

(71) Applicant: Changde Jizhi Biological Technology Co., Ltd, Changde (CN)

(72) Inventor: Xinqiao He, Changde (CN)

(73) Assignee: Changde Jizhi Biological Technology Co., Ltd, Changde (CN)

( * ) Notice: Subject to any disclaimer, the term of this patent is extended or adjusted under 35 U.S.C. 154(b) by 468 days.

(21) Appl. No.: 18/406,049

(22) Filed: Jan. 5, 2024

(65) Prior Publication Data

US 2025/0222051 A1 Jul. 10, 2025

(51) Int. Cl.

| | |
|---|---|
| ***A61K 36/00*** | (2006.01) |
| ***A61K 31/197*** | (2006.01) |
| ***A61K 31/685*** | (2006.01) |
| ***A61K 33/30*** | (2006.01) |
| ***A61K 35/57*** | (2015.01) |
| ***A61K 35/586*** | (2015.01) |
| ***A61K 35/60*** | (2006.01) |
| ***A61K 35/616*** | (2015.01) |
| ***A61K 35/618*** | (2015.01) |
| ***A61K 36/068*** | (2006.01) |
| ***A61K 36/07*** | (2006.01) |
| ***A61K 36/185*** | (2006.01) |
| ***A61K 36/258*** | (2006.01) |
| ***A61K 36/46*** | (2006.01) |
| ***A61K 36/605*** | (2006.01) |
| ***A61K 36/815*** | (2006.01) |
| ***A61K 36/82*** | (2006.01) |
| ***A61K 36/8945*** | (2006.01) |
| ***A61K 36/8984*** | (2006.01) |
| ***A61K 39/395*** | (2006.01) |
| ***A61P 35/00*** | (2006.01) |

(52) U.S. Cl.

CPC .......... *A61K 36/068* (2013.01); *A61K 31/197* (2013.01); *A61K 31/685* (2013.01); *A61K 33/30* (2013.01); *A61K 35/57* (2013.01); *A61K 35/586* (2013.01); *A61K 35/60* (2013.01); *A61K 35/616* (2013.01); *A61K 35/618* (2013.01); *A61K 36/07* (2013.01); *A61K 36/185* (2013.01); *A61K 36/258* (2013.01); *A61K 36/46* (2013.01); *A61K 36/605* (2013.01); *A61K 36/815* (2013.01); *A61K 36/82* (2013.01); *A61K 36/8945* (2013.01); *A61K 36/8984* (2013.01); *A61K 39/39516* (2013.01); *A61P 35/00* (2018.01); *A61K 2236/19* (2013.01); *A61K 2236/331* (2013.01); *A61K 2236/53* (2013.01)

(58) Field of Classification Search

CPC .................................................. A61K 36/068

See application file for complete search history.

(56) References Cited

FOREIGN PATENT DOCUMENTS

CN 106071723 A * 11/2016

* cited by examiner

*Primary Examiner* — Qiuwen Mi

(74) *Attorney, Agent, or Firm* — Hemisphere Law, PLLC

(57) ABSTRACT

A multivitamin for adjuvant treatment of a tumor, and a preparation method and an application thereof are provided, relating to the field of biomedical technologies. The multivitamin is made from raw materials: *Cordyceps sinensis, Dendrobium officinale* Kimura et Migo, red ginseng, *Eucommia ulmoides* male flower, shark fin, *Lycium chinense*, okra, mulberry, Chinese yam, Edible bird's nest, Abalone, sea cucumber, shark cartilage, turtle rim, gamma globulin, non-transgenic soybean lecithin, camellia oil, seabuckthorn seed oil, *Lentinus edodes* peptides, amino acids, and nano zinc oxide. In this situation, free radicals and killed bacteria and viruses in the body can be discharged, and nanoscale active lysozymes enter cells and tissues in the body to assist the immune system to kill bacteria and viruses. By eating the multivitamin, and supplementing and balancing nutrition, the immune function of the body can be quickly restored.

20 Claims, No Drawings

MULTIVITAMIN FOR ADJUVANT TREATMENT OF TUMOR, AND PREPARATION METHOD AND APPLICATION THEREOF

TECHNICAL FIELD

The disclosure relates to the field of biomedical technologies, and more particularly to a multivitamin for adjuvant treatment of a tumor, and a preparation method and an application thereof.

BACKGROUND

There are many studies and theories about cancer, and most people accept the theory of authoritative experts that cancer is caused by genetic mutations that cause cells to grow out of control. In medicine, cancer refers to a malignant tumor originating from epithelial tissue, which is the most common type of malignant tumor. Correspondingly, malignant tumors originating from mesenchymal tissue are collectively called sarcomas. There are few malignant tumors that are not named according to the above principles, such as nephroblastoma, malignant teratoma, and so on. Generally speaking, the term "cancer" is traditionally used to refer to all malignant tumors. Cancer has biological characteristics such as abnormal cell differentiation and proliferation, uncontrolled growth, invasion and metastasis. The occurrence of cancer is a multi-factor and multi-step complex process, which is divided into three processes: carcinogenesis, cancer promotion and evolution, and is closely related to smoking, infection, occupational exposure, environmental pollution, unreasonable diet and genetic factors.

There are many kinds of malignant tumors, with different natures and types, different tissues and organs involved, different stages of illness and different responses to various treatments. Therefore, most patients need comprehensive treatment. The so-called comprehensive treatment refers to the comprehensive use of surgery, chemotherapy, radiotherapy, immunotherapy, traditional Chinese medicine treatment, interventional therapy, microwave therapy and other means according to the patient's physical condition, pathological type of tumor, and the scope of invasion, in order to greatly improve the cure rate and improve the quality of life of patients.

In medicine, it is also said that a tumor is cancer cells growing in the human body, the growth of which is not controlled by the human body, and it needs to be killed by means of chemicals, radiation, etc. According to the research of scientific researchers, there are about 40 trillion to 60 trillion human cells, and the average diameter of the cells is between 5-200 microns. Except for mature red blood cells (also referred to as erythrocytes) and platelets, all cells have at least one nucleus, which is the control center for regulating cell life activities and controlling division, differentiation, inheritance and variation. Human cells are exclusive, as long as they are not transplanted, the cells in the human body are all their own cells. There are necrotic cells in the process of metabolism. After infection, inflammation will occur, which will redden and diffuse the area of inflammation. Redden and swelling are caused by inflammation, which should not be that the growth of cancer cells is out of control and should not kill "cancer cells". In this situation, bacteria and viruses should be killed, and after anti-inflammation, the tumor will naturally disappear. It is only because the current medicine has not yet developed drugs, equipment and methods that can target and kill bacteria and viruses in cell tissues without harming human cells.

Undoubtedly, cancer is actually caused by endogenous diseases and inflammation. It is closely related to nutritional deficiency, deficiency of qi and blood, poor blood circulation, decreased immunity and blocked self-healing function. In turn, it is understood that the blocked self-healing function is related to the decrease of immune ability, the decrease of immune ability is related to the poor blood circulation, the poor blood circulation is related to the deficiency of qi and blood, and the deficiency of qi and blood is related to the nutritional deficiency. Therefore, cancer is a result of extreme nutritional deficiencies. All diseases are divided into acute diseases and chronic diseases. The cause of acute diseases is very clear, because one injury is enough to cause acute damage to the body, such as being hit by a car, slashed by a knife, bacterial infection, etc. Chronic disease is a process of frequent mild injury, which accumulates from mild injury to severe injury. For example, it's not because of a few more bites of food or a little more alcohol or a few more cigarettes on any given day, but it's a little bit of damage to the liver every day, and eventually, the damage finally reveals itself. Chronic injury is a repetitive process in which the body is injured and repaired at the same time, and the repair needs nutrients as raw materials. Therefore, all chronic injuries are at the expense of consuming nutrients, until the nutrients in the body are exhausted and can no longer be repaired, the disease will slowly show up. All chronic diseases, including cancer, are essentially caused by extreme lack and imbalance of nutrients, regardless of the cause. Cancer may be formed as cells die and grow, grow and die again. There is chronic inflammation in the body, and cells proliferate in batches. When chromosome or gene abnormalities occur, due to lack of nutrients, cells cannot start repair or suicide mechanism in time, will lead to chromosome or gene abnormalities handed down from generation to generation, each generation of proliferation may produce new chromosome or gene abnormalities. In this situation, the range of chromosome or gene abnormality will continue to expand, the balance of genes in the nucleus will be disrupted, and abnormal excessive proliferation of cells will occur, that is, the range of inflammation will continue to expand, and cancer will occur.

Since the development of medicine, there are several kinds of drugs to treat tumors, including chemical drugs and biological drugs, etc. As a means of adjuvant therapy, traditional Chinese medicine plays an important role in lifting weight. Therefore, it is of great significance to study and develop a new composition to improve the curative effect of chemical drugs or biological drugs and reduce their side effects.

SUMMARY

The main purpose of the disclosure is to provide a multivitamin for adjuvant treatment of a tumor, and a preparation method and an application thereof. In the disclosure, free radicals and killed bacteria and viruses in the body can be discharged, and nanoscale active lysozymes enter cells and tissues in the body to assist the immune system to kill bacteria and viruses. By eating the multivitamin, and supplementing and balancing nutrition, the immune function of the body can be quickly restored.

Compared with the related art, technical solutions of the disclosure are as follows.

Specifically, in an aspect, a multivitamin for adjuvant treatment of a tumor is made from raw materials in parts by weight as follows: 5-15 parts of *Cordyceps sinensis,* 5-15 parts of *Dendrobium officinale* Kimura et Migo, 5-15 parts of red ginseng, 5-15 parts of *Eucommia ulmoides* male flower, 5-15 parts of shark fin, 5-15 parts of *Lycium chinense,* 5-15 parts of okra, 5-15 parts of mulberry, 5-15 parts of Chinese yam, 5-15 parts of Edible bird's nest, 5-15 parts of Abalone, 5-15 parts of sea cucumber, 5-15 parts of shark cartilage, 5-15 parts of turtle rim, 10-20 parts of gamma globulin, 10-20 parts of non-transgenic soybean lecithin, 20-40 parts of camellia oil, 10-20 parts of seabuckthorn seed oil, 5 parts of *Lentinus edodes* peptides, 5 parts of amino acids, and 0.5 parts of nano zinc oxide.

In an embodiment, the multivitamin is specifically made from the raw materials in parts by weight as follows: 5 parts of *Cordyceps sinensis,* 5 parts of *Dendrobium officinale* Kimura et Migo, 5 parts of red ginseng, 5 parts of *Eucommia ulmoides* male flower, 5 parts of shark fin, 5 parts of *Lycium chinense,* 5 parts of okra, 5 parts of mulberry, 5 parts of Chinese yam, 5 parts of Edible bird's nest, 5 parts of Abalone, 5 parts of sea cucumber, 5 parts of shark cartilage, 5 parts of turtle rim, 10 parts of gamma globulin, 10 parts of non-transgenic soybean lecithin, 20 parts of camellia oil, 10 parts of seabuckthorn seed oil, 5 parts of *Lentinus edodes* peptides, 5 parts of amino acids, and 0.5 parts of nano zinc oxide.

In an embodiment, the multivitamin is specifically made from the raw materials in parts by weight as follows: 10 parts of *Cordyceps sinensis,* 10 parts of *Dendrobium officinale* Kimura et Migo, 10 parts of red ginseng, 10 parts of *Eucommia ulmoides* male flower, 10 parts of shark fin, 10 parts of *Lycium chinense,* 10 parts of okra, 10 parts of mulberry, 10 parts of Chinese yam, 10 parts of Edible bird's nest, 10 parts of Abalone, 10 parts of sea cucumber, 10 parts of shark cartilage, 10 parts of turtle rim, 15 parts of gamma globulin, 15 parts of non-transgenic soybean lecithin, 30 parts of camellia oil, 15 parts of seabuckthorn seed oil, 5 parts of *Lentinus edodes* peptides, 5 parts of amino acids, and 0.5 parts of nano zinc oxide.

In an embodiment, the multivitamin is specifically made from the raw materials in parts by weight as follows: 15 parts of *Cordyceps sinensis,* 15 parts of *Dendrobium officinale* Kimura et Migo, 15 parts of red ginseng, 15 parts of *Eucommia ulmoides* male flower, 15 parts of shark fin, 15 parts of *Lycium chinense,* 15 parts of okra, 15 parts of mulberry, 15 parts of Chinese yam, 15 parts of Edible bird's nest, 15 parts of Abalone, 15 parts of sea cucumber, 15 parts of shark cartilage, 15 parts of turtle rim, 20 parts of gamma globulin, 20 parts of non-transgenic soybean lecithin, 40 parts of camellia oil, 20 parts of seabuckthorn seed oil, 5 parts of *Lentinus edodes* peptides, 5 parts of amino acids, and 0.5 parts of nano zinc oxide.

In another aspect, a preparation method of the multivitamin includes the following steps: step 1: adding water to the *Cordyceps sinensis*, the *Dendrobium officinale* Kimura et Migo, the red ginseng, the *Eucommia ulmoides* male flower, the *Lycium chinense*, the okra, the mulberry, and the Chinese yam to obtain a first mixture, with a water addition of 20-30 times a weight of the *Cordyceps sinensis*, decocting the first mixture for 150-200 minutes to obtain a decocted mixture, filtering the decocted mixture with an 800-mesh filter to obtain a mixed nutrient solution, putting the mixed nutrient solution into a fermentation tank, adding mucor and brown sugar into the fermentation tank for fermentation, taking out a fermented product after 80-100 days of fermentation, adding anhydrous ethanol into the fermented product with an ethanol addition of 30%-50% of a weight of the mixed nutrient solution, standing the fermented product added with the anhydrous ethanol for 12-24 hours, and filtering the stood product to obtain a filtrate for later use; step 2: adding water to the shark fin, the Edible bird's nest, the Abalone, the sea cucumber, the shark cartilage, the turtle rim to obtain a second mixture, with a water addition of 15-25 times of a weight of the shark fin, decocting the second mixture for 40-56 hours to obtain a mixed nutritional paste, and then drying the mixed nutritional paste to obtain small-molecule mixed peptides; and step 3: mixing the filtrate for later use obtained in the step 1 and the small-molecule mixed peptides obtained in the step 2 with the gamma globulin, the non-transgenic soybean lecithin, the camellia oil, the seabuckthorn seed oil, the *Lentinus edodes* peptides, the amino acids, and the nano zinc oxide to obtain a third mixture, and uniformly stirring the third mixture to obtain the multivitamin.

In still another aspect, an application of the multivitamin in preparing drugs for adjuvant treatment of tumors.

In an embodiment, an addition amount of the mucor is in a range of 0.25% to 0.65% of the weight of the mixed nutrient solution.

In an embodiment, an addition amount of the brown sugar is in a range of 5% to 8% of the weight of the mixed nutrient solution.

The disclosure has beneficial effects as follows.

The multivitamin extracted from various rare Chinese medicines, plants and foods contains various vitamins, trace elements, rich protein and minerals, and can quickly balance nutrition, replenish energy, enhance immunity, kill bacteria and viruses by relying on its own immune system and self-healing function, repair damaged cells, and promote cell regeneration and metabolism. In addition, using small-molecule water vapor thermal therapy (WVTT), nanoscale active lysozymes extracted from protein after multiple fermentations are added into small molecules of water, and patients are subjected to the water vapor thermal therapy, capillaries are expanded, free radicals and killed bacteria and viruses in the body are discharged, and the nanoscale active lysozymes enter the cell tissues in the body to assist the immune system in killing bacteria and viruses. By consuming multivitamins, nutrition can be supplemented and balanced, and the immune function of the body can be quickly restored.

DETAILED DESCRIPTION OF EMBODIMENTS

In order to enable those skilled in the art better understand technical solutions of the disclosure, the technical solutions in embodiments of the disclosure are described clearly and completely below. Apparently, the described embodiments are only some of the embodiments of the disclosure, and not all of them. Based on the embodiments in the disclosure, all other embodiments obtained by those skilled in the art without creative work should belong to the scope of protection of the disclosure.

Embodiment 1

A multivitamin for adjuvant treatment of tumors includes the following raw materials: 100 grams (g) of *Cordyceps sinensis,* 100 g of *Dendrobium officinale* Kimura et Migo, 100 g of red ginseng, 100 g of *Eucommia ulmoides* male flower, 100 g of shark fin, 100 g of *Lycium chinense,* 100 g of okra, 100 g of mulberry, 100 g of Chinese yam, 100 g of Edible bird's nest, 100 g of Abalone, 100 g of sea cucumber, 100 g of shark cartilage, 100 g of turtle rim, 150 g of gamma globulin, 150 g of non-transgenic soybean lecithin, 300 g of camellia oil, 150 g of seabuckthorn seed oil, 50 g of *Lentinus edodes* peptides, 50 g of amino acids, and 5 g of nano zinc oxide.

Step 1: water is added to the *Cordyceps sinensis*, the *Dendrobium officinale* Kimura et Migo, the red ginseng, the *Eucommia ulmoides* male flower, the *Lycium chinense*, the okra, the mulberry, and the Chinese yam to obtain a first mixture, with a water addition of 20 times a weight of the *Cordyceps sinensis*. The first mixture is decocted for 150 minutes to obtain a decocted mixture, the decocted mixture is filtered with an 800-mesh filter to obtain a mixed nutrient solution. The mixed nutrient solution is put into a fermentation tank, mucor and brown sugar are added into the fermentation tank for fermentation, with an addition amount of the mucor of 0.25% of the weight of the mixed nutrient solution and an addition amount of the brown sugar of 5% of the weight of the mixed nutrient solution. A fermented product after 80 days of fermentation is taken out, and added with anhydrous ethanol into the fermented product with an ethanol addition of 30% of the weight of the mixed nutrient solution, standing the fermented product added with the anhydrous ethanol for 12 hours, and the stood product is filtered to obtain a filtrate for later use.

Step 2: water is added to the shark fin, the Edible bird's nest, the Abalone, the sea cucumber, the shark cartilage, the turtle rim to obtain a second mixture, with a water addition of 15 times of a weight of the shark fin, the second mixture is decocted for 40 hours to obtain a mixed nutritional paste, and then the mixed nutritional paste is dried to obtain small-molecule mixed peptides.

Step 3: the filtrate for later use obtained in the step 1 and the small-molecule mixed peptides obtained in the step 2 are mixed with the gamma globulin, the non-transgenic soybean lecithin, the camellia oil, the seabuckthorn seed oil, the *Lentinus edodes* peptides, the amino acids, and the nano zinc oxide to obtain a third mixture, and uniformly stirring the third mixture to obtain the multivitamin.

Embodiment 2

A multivitamin for adjuvant treatment of tumors includes the following raw materials: 50 g of *Cordyceps sinensis,* 50 g of *Dendrobium officinale* Kimura et Migo, 50 g of red ginseng, 50 g of *Eucommia ulmoides* male flower, 50 g of shark fin, 50 g of *Lycium chinense,* 50 g of okra, 50 g of mulberry, 50 g of Chinese yam, 50 g of Edible bird's nest, 50 g of Abalone, 50 g of sea cucumber, 50 g of shark cartilage, 50 g of turtle rim, 100 g of gamma globulin, 100 g of non-transgenic soybean lecithin, 200 g of camellia oil, 100 g of seabuckthorn seed oil, 50 g of *Lentinus edodes* peptides, 50 g of amino acids, and 5 g of nano zinc oxide.

Step 1: water is added to the *Cordyceps sinensis*, the *Dendrobium officinale* Kimura et Migo, the red ginseng, the *Eucommia ulmoides* male flower, the *Lycium chinense*, the okra, the mulberry, and the Chinese yam to obtain a first mixture, with a water addition of 25 times a weight of the *Cordyceps sinensis*. The first mixture is decocted for 180 minutes to obtain a decocted mixture, the decocted mixture is filtered with an 800-mesh filter to obtain a mixed nutrient solution. The mixed nutrient solution is put into a fermentation tank, mucor and brown sugar are added into the fermentation tank for fermentation, with an addition amount of the mucor of 0.45% of the weight of the mixed nutrient solution and an addition amount of the brown sugar of 6% of the weight of the mixed nutrient solution. A fermented product after 90 days of fermentation is taken out, and added with anhydrous ethanol into the fermented product with an ethanol addition of 40% of the weight of the mixed nutrient solution, standing the fermented product added with the anhydrous ethanol for 18 hours, and the stood product is filtered to obtain a filtrate for later use.

Step 2: water is added to the shark fin, the Edible bird's nest, the Abalone, the sea cucumber, the shark cartilage, the turtle rim to obtain a second mixture, with a water addition of 20 times of a weight of the shark fin, the second mixture is decocted for 48 hours to obtain a mixed nutritional paste, and then the mixed nutritional paste is dried to obtain small-molecule mixed peptides.

Step 3: the filtrate for later use obtained in the step 1 and the small-molecule mixed peptides obtained in the step 2 are mixed with the gamma globulin, the non-transgenic soybean lecithin, the camellia oil, the seabuckthorn seed oil, the *Lentinus edodes* peptides, the amino acids, and the nano zinc oxide to obtain a third mixture, and uniformly stirring the third mixture to obtain the multivitamin.

Embodiment 3

A multivitamin for adjuvant treatment of tumors includes the following raw materials: 150 g of *Cordyceps sinensis,* 150 g of *Dendrobium officinale* Kimura et Migo, 150 g of red ginseng, 150 g of *Eucommia ulmoides* male flower, 150 g of shark fin, 150 g of *Lycium chinense,* 150 g of okra, 150 g of mulberry, 150 g of Chinese yam, 150 g of Edible bird's nest, 150 g of Abalone, 150 g of sea cucumber, 150 g of shark cartilage, 150 g of turtle rim, 200 g of gamma globulin, 200 g of non-transgenic soybean lecithin, 400 g of camellia oil, 200 g of seabuckthorn seed oil, 50 g of *Lentinus edodes* peptides, 50 g of amino acids, and 5 g of nano zinc oxide.

Step 1: water is added to the *Cordyceps sinensis*, the *Dendrobium officinale* Kimura et Migo, the red ginseng, the *Eucommia ulmoides* male flower, the *Lycium chinense*, the okra, the mulberry, and the Chinese yam to obtain a first mixture, with a water addition of 30 times a weight of the *Cordyceps sinensis*. The first mixture is decocted for 200 minutes to obtain a decocted mixture, the decocted mixture is filtered with an 800-mesh filter to obtain a mixed nutrient solution. The mixed nutrient solution is put into a fermentation tank, mucor and brown sugar are added into the fermentation tank for fermentation, with an addition amount of the mucor of 0.65% of the weight of the mixed nutrient solution and an addition amount of the brown sugar of 8% of the weight of the mixed nutrient solution. A fermented product after 100 days of fermentation is taken out, and added with anhydrous ethanol into the fermented product with an ethanol addition of 50% of the weight of the mixed nutrient solution, standing the fermented product added with the anhydrous ethanol for 24 hours, and the stood product is filtered to obtain a filtrate for later use.

Step 2: water is added to the shark fin, the Edible bird's nest, the Abalone, the sea cucumber, the shark cartilage, the turtle rim to obtain a second mixture, with a water addition of 25 times of a weight of the shark fin, the second mixture is decocted for 56 hours to obtain a mixed nutritional paste, and then the mixed nutritional paste is dried to obtain small-molecule mixed peptides.

Step 3: the filtrate for later use obtained in the step 1 and the small-molecule mixed peptides obtained in the step 2 are mixed with the gamma globulin, the non-transgenic soybean lecithin, the camellia oil, the seabuckthorn seed oil, the *Lentinus edodes* peptides, the amino acids, and the nano zinc oxide to obtain a third mixture, and uniformly stirring the third mixture to obtain the multivitamin.

Comparative Embodiment 1

The difference between this comparative embodiment and the embodiment 1 is only the lack of *Cordyceps sinensis* and *Dendrobium officinale* Kimura et Migo, and other raw materials and the preparation method are the same as the embodiment 1.

Comparative Embodiment 2

The difference between this comparative embodiment and the embodiment 1 is only the lack of sea cucumber, Edible bird's nest and Abalone, and other raw materials and the preparation method are the same as the embodiment 1.

Comparative Embodiment 3

The difference between this comparative embodiment and the embodiment 1 is only the lack of camellia oil, seabuckthorn seed oil and *Lentinus edodes* peptides, and other raw materials and the preparation method are the same as the embodiment 1.

Comparative Embodiment 4

The difference between this comparative embodiment and the embodiment 1 is only the lack of *Lycium chinense*, okra, mulberry and Chinese yam, and other raw materials and the preparation method are the same as the embodiment 1.

Comparative Embodiment 5

The difference between this comparative embodiment and the embodiment 1 is only the lack of shark cartilage and gamma globulin, and other raw materials and the preparation method are the same as the embodiment 1.

Experimental Embodiment 1

The anti-tumor effect of the product of the disclosure on a Hepatoma-22 (H22) mouse model of live cancer is studied.

Experimental materials, reagents, drugs and equipment are as follows.

Positive control drug: oxaliplatin.

Test drug groups: embodiments 1, 2 and 3 and comparative embodiments 1-5 of the disclosure.

Animals and preparation of tumors are as follows. BALB/c male mice are adopted, weighing 18-22 g. The mice are fed in specific-pathogen free (SPF) grade animal house, with temperature of 20-25° C., relative humidity of 40%-70%, 6 mice per cage, illumination time of 12 h, regular and quantitative addition of feed, free drinking water, and daily replacement of padding.

Transplanted tumor cells: $10^6$ mouse H22 hepatoma cells are injected into abdominal cavity for passage, and the hepatoma cells are collected after 7-10 days for subcutaneous inoculation.

Experimental methods of tumor passage preservation for in vivo tumor inhibition effect evaluation: H22 hepatoma mice are inoculated intraperitoneally and the ascites is taken for passage and preservation.

Tumor inoculation: H22 hepatocellular carcinoma bearing mice on the $10^{th}$ day of ascites passage are taken, the mice are killed by cervical vertebra removal, the abdominal skin is disinfected, milky white ascites is absorbed with a sterile syringe, and the concentration of tumor cells is adjusted to $1\times10^6$ cells per milliliter (mL) with normal saline for injection. The right armpit skin of BALB/c mice is disinfected with alcohol cotton balls, 0.2 mL of the tumor cell suspension is inoculated subcutaneously, and the mice are raised routinely.

Grouping and administration: tumor-bearing mice, randomly grouped by body weight, are: model control group, oxaliplatin group, oxaliplatin+embodiment 1 group, oxaliplatin+embodiment 2 group, oxaliplatin+embodiment 3 group, oxaliplatin+comparative embodiment 1 group, oxaliplatin+comparative embodiment 2 group, oxaliplatin+comparative embodiment 3 group, oxaliplatin+comparative embodiment 4 group, and oxaliplatin+comparative embodiment 5 group. The mice are administered on the second day after tumor inoculation, and the oxaliplatin group is administered only once on the second day after tumor inoculation (tail vein administration of 15 milligrams per kilogram abbreviated as mg/kg). The model control group is intragastrically administered normal saline once daily, and the rest groups are administered oxaliplatin once on the second day after tumor inoculation (tail vein administration of 15 mg/kg). After 8 hours of administration, the mice are administered 0.45 grams per kilogram (g/kg) of products of the embodiment 1, the embodiment 2, the embodiment 3, and the comparative embodiments 1-5 by intragastric administration. On the third day, after 2 hours of feeding in the morning, the products of the embodiment 1, the embodiment 2, the embodiment 3, and the comparative embodiments 1-5 are administered continuously for 10 days. After 24 hours of the last administration, the mice are sacrificed by cervical dislocation, and the tumor tissues are stripped and weighed. The curative effect is evaluated by tumor weight inhibition rate (%), and analysis of variance (ANOVA) test is used for statistical comparison between groups.

Experimental results: as shown in Table 1.

TABLE 1

Comparison of tumor inhibition effects of products of the disclosure

| Group | Number of animals | Weight Start | Weight Final | Tumor weight (g) | Inhibition rate (%) |
|---|---|---|---|---|---|
| Model control group | 10 | 21.47 ± 0.94 | 23.79 ± 1.06 | 2.29 ± 0.26 | — |
| Oxaliplatin group | 10 | 20.09 ± 1.08 | 20.44 ± 1.23 | 1.14 ± 0.29** | 50.22 |
| Oxaliplatin + Embodiment 1 group | 10 | 21.38 ± 1.28 | 22.97 ± 0.88 | 0.79 ± 0.35**# | 65.50 |
| Oxaliplatin + | 10 | 20.38 ± 1.14 | 21.88 ± 1.17 | 0.83 ± 0.29**# | 69.15 |

TABLE 1-continued

Comparison of tumor inhibition effects of products of the disclosure

| Group | Number of animals | Weight Start | Weight Final | Tumor weight (g) | Inhibition rate (%) |
|---|---|---|---|---|---|
| Embodiment 2 group | | | | | |
| Oxaliplatin + Embodiment 3 group | 10 | 21.48 ± 1.27 | 21.48 ± 1.27 | 0.57 ± 0.07**## | 73.54 |
| Oxaliplatin + Comparative Embodiment 1 group | 10 | 21.50 ± 1.17 | 21.72 ± 1.17 | 1.02 ± 0.26** | 55.9 |
| Oxaliplatin + Comparative Embodiment 2 group | 10 | 20.35 ± 0.89 | 20.70 ± 1.29 | 10.9 ± 0.18** | 52.24 |
| Oxaliplatin + Comparative Embodiment 3 group | 10 | 20.36 ± 0.94 | 20.70 ± 1.17 | 1.07 ± 0.22** | 51.25 |
| Oxaliplatin + Comparative Embodiment 4 group | 10 | 21.15 ± 1.04 | 21.47 ± 0.81 | 1.16 ± 0.14** | 56.23 |
| Oxaliplatin + Comparative Embodiment 5 group | 10 | 21.32 ± 1.04 | 21.56 ± 0.94 | 1.05 ± 0.20** | 49.59 |

Note:
compared with the model control group,
***p < 0.001,
***P < 0.01,
*p < 0.05.
Compared with the oxaliplatin group,
P < 0.01,
#P < 0.05.

In summary, the experiment shows that the combination of oxaliplatin and the product of the disclosure can reduce the tumor weight of mice when used in mice with tumors, indicating that the product of the disclosure can promote the effect of oxaliplatin in killing cancer cells and improve the curative effect of oxaliplatin. However, after the ingredients such as *Cordyceps sinensis* and *Dendrobium officinale* Kimura et Migo are removed from the raw materials of the product (comparative embodiment 1-5), the effect of improving the curative effect is not significant, which fully shows that the raw materials of the product cannot be simply analyzed, but form a whole effect after combination, and various raw materials of this effect are intertwined to jointly play a synergistic role.

Experimental Embodiment 2

The anti-tumor effect of the products on three kinds of nude mice transplanted tumor is studied and tested.

Experimental animals: BLAB/c female nude mice, 6-7 weeks old, weighing 18-20 g.

Subcutaneous tumor cell inoculation in mice: Human lung cancer cells (A549), human ovarian cancer cells (Skov-3) and human cervical cancer epithelial cells (Hela) in logarithmic growth phase are taken and made into cell suspension ($1\times10^7$ cells/mL) with phosphate buffered saline (PBS), each mouse is inoculated with $2\times10^6$ cells, the inoculation volume is 200 microliters (μL), and then inoculated subcutaneously in the armpit of BLAB/c nude mice. The selected tumor tissues are put into a glass homogenizer, ground with sterile physiological saline, filtered into a single cell suspension through a sieve, and the number of living cells is counted by trypan blue staining. Each nude mouse is inoculated with 200 μL cell suspension (including $1\times10^6$ cells) under its armpit.

Experimental grouping and methods: nude mice with the same tumor size are selected, and the nude mice are weighed and randomly divided into groups. The nude mice inoculated with each tumor cell are divided into model control group, oxaliplatin group, oxaliplatin+embodiment 1 group, oxaliplatin+embodiment 2 group, oxaliplatin+embodiment 3 group. The drug concentration and specific grouping are as follows. The model control group is intragastrically administered with 200 μL normal saline once a day, the mice are administered once on the second day after tumor inoculation. The oxaliplatin group is administered only once on the second day after tumor inoculation (tail vein administration of 15 mg/kg). The model control group is administered normal saline once a day, and the rest groups are administered oxaliplatin once on the second day after tumor inoculation (tail vein administration of 15 mg/kg). After 8 hours of administration, the mice are administered 0.45 g/kg of products of the embodiment 1, the embodiment 2, the embodiment 3 by intragastric administration. On the third day, after 2 hours of feeding in the morning, the products of the embodiment 1, the embodiment 2, and the embodiment 3 are administered continuously for 10 days. After 24 hours of the last administration, the tumor mass is taken out, the tumor weight is measured and the tumor inhibition rate is calculated.

Experimental results show that the products of the disclosure have inhibition effect on A549 nude mice transplanted tumor. The experimental results are shown in Table 2.

TABLE 2

Experimental results ($\overline{X}$ ± SD) of inhibition effect of products of the disclosure on A549 nude mice transplanted tumor

| Group | Number of animals | Tumor weight (g) | Inhibition rate (%) |
|---|---|---|---|
| Model control group | 8 | 2.33 ± 0.24 | — |
| Oxaliplatin group | 8 | 0.98 ± 0.32** | 58.25 |
| Oxaliplatin + Embodiment 1 group | 8 | 0.74 ± 0.25**# | 68.56 |
| Oxaliplatin + Embodiment 2 group | 8 | 0.72 ± 0.18**# | 67.26 |
| Oxaliplatin + Embodiment 3 group | 8 | 0.53 ± 0.17***## | 77.82 |

Note:
compared with the model control group,
***p < 0.001,
***P < 0.01,
*p < 0.05.
Compared with the oxaliplatin group,
P < 0.01,
#P < 0.05.

The products of the disclosure have inhibition effect on transplanted tumor of Skov-3 nude mice transplanted tumor. The experimental results are shown in Table 3.

TABLE 3

Experimental results ($\overline{X}$ ± SD) of inhibition effect of products of the disclosure on Skov-3 nude mice transplanted tumor

| Group | Number of animals | Tumor weight (g) | Inhibition rate (%) |
|---|---|---|---|
| Model control group | 8 | 3.31 ± 0.24 | — |
| Oxaliplatin group | 8 | 1.78 ± 0.33** | 45.25 |
| Oxaliplatin + Embodiment 1 group | 8 | 1.35 ± 0.21**# | 52.59 |
| Oxaliplatin + Embodiment 2 group | 8 | 1.42 ± 0.18**# | 54.78 |
| Oxaliplatin + Embodiment 3 group | 8 | 0.93 ± 0.17***## | 70.98 |

Note:
compared with the model control group,
***p < 0.001,
***P < 0.01,
*p < 0.05.
Compared with the oxaliplatin group,
P < 0.01,
#P < 0.05.

The products of the disclosure have inhibition effect on Hela nude mice transplanted tumor. The experimental results are shown in Table 4.

TABLE 4

Experimental results ($\overline{X}$ ± SD) of inhibition effect of products of the disclosure on Hela nude mice transplanted tumor

| Group | Number of animals | Tumor weight (g) | Inhibition rate (%) |
|---|---|---|---|
| Model control group | 8 | 3.31 ± 0.24 | — |
| Oxaliplatin group | 8 | 1.78 ± 0.33** | 45.25 |
| Oxaliplatin + Embodiment 1 group | 8 | 1.35 ± 0.21**# | 52.59 |
| Oxaliplatin + Embodiment 2 group | 8 | 1.42 ± 0.18**# | 54.78 |
| Oxaliplatin + Embodiment 3 group | 8 | 0.93 ± 0.17***## | 70.98 |

Note:
compared with the model control group,
***p < 0.001,
***P < 0.01,
*p < 0.05.
Compared with the oxaliplatin group,
P < 0.01,
#P < 0.05.

In conclusion, the above experiments show that oxaliplatin has a good effect on killing cancer cells and can reduce the weight of tumor. After the product of the disclosure is used in combination with oxaliplatin, cancer cells can be killed more significantly, and the weight of tumor can be reduced rapidly, thus indicating that the multivitamin or the combination of multivitamin and toxin-lytic biomimetic enzyme of the disclosure can assist in the treatment of tumor. However, after removing some raw materials of the multivitamin of the disclosure, it cannot significantly reduce the tumor weight, which further shows that the raw material composition of the disclosure is an organic whole.

The above is only the illustrated embodiments of the disclosure, and it should be noted that those skilled in the art can make several improvements and embellishments without departing from the principle of the disclosure, and these improvements and embellishments should also be regarded as the protection scope of the disclosure.

What is claimed is:

1. A composition for adjuvant treatment of a tumor, wherein the composition is made from raw materials in parts by weight as follows:

5-15 parts of *Cordyceps sinensis,* 5-15 parts of *Dendrobium officinale* Kimura et Migo, 5-15 parts of red ginseng, 5-15 parts of *Eucommia ulmoides* male flower, 5-15 parts of shark fin, 5-15 parts of *Lycium chinense,* 5-15 parts of okra, 5-15 parts of mulberry, 5-15 parts of Chinese yam, 5-15 parts of Edible bird's nest, 5-15 parts of Abalone, 5-15 parts of sea cucumber, 5-15 parts of shark cartilage, 5-15 parts of turtle rim, 10-20 parts of gamma globulin, 10-20 parts of non-transgenic soybean lecithin, 20-40 parts of camellia oil, 10-20 parts of seabuckthorn seed oil, 5 parts of *Lentinus edodes* peptides, 5 parts of amino acids, and 0.5 parts of nano zinc oxide.

2. The composition as claimed in claim 1, wherein the composition is specifically made from the raw materials in parts by weight as follows:

5 parts of *Cordyceps sinensis,* 5 parts of *Dendrobium officinale* Kimura et Migo, 5 parts of red ginseng, 5 parts of *Eucommia ulmoides* male flower, 5 parts of shark fin, 5 parts of *Lycium chinense,* 5 parts of okra, 5 parts of mulberry, 5 parts of Chinese yam, 5 parts of Edible bird's nest, 5 parts of Abalone, 5 parts of sea cucumber, 5 parts of shark cartilage, 5 parts of turtle rim, 10 parts of gamma globulin, 10 parts of non-transgenic soybean lecithin, 20 parts of camellia oil, 10 parts of seabuckthorn seed oil, 5 parts of *Lentinus edodes* peptides, 5 parts of amino acids, and 0.5 parts of nano zinc oxide.

3. The composition as claimed in claim 1, wherein the composition is specifically made from raw materials in parts by weight as follows:

10 parts of *Cordyceps sinensis,* 10 parts of *Dendrobium officinale* Kimura et Migo, 10 parts of red ginseng, 10 parts of *Eucommia ulmoides* male flower, 10 parts of shark fin, 10 parts of *Lycium chinense,* 10 parts of okra, 10 parts of mulberry, 10 parts of Chinese yam, 10 parts of Edible bird's nest, 10 parts of Abalone, 10 parts of sea cucumber, 10 parts of shark cartilage, 10 parts of turtle rim, 15 parts of gamma globulin, 15 parts of non-transgenic soybean lecithin, 30 parts of camellia oil, 15 parts of seabuckthorn seed oil, 5 parts of *Lentinus edodes* peptides, 5 parts of amino acids, and 0.5 parts of nano zinc oxide.

4. The composition as claimed in claim 1, wherein the composition is specifically made from raw materials in parts by weight as follows:

15 parts of *Cordyceps sinensis,* 15 parts of *Dendrobium officinale* Kimura et Migo, 15 parts of red ginseng, 15 parts of *Eucommia ulmoides* male flower, 15 parts of shark fin, 15 parts of *Lycium chinense,* 15 parts of okra, 15 parts of mulberry, 15 parts of Chinese yam, 15 parts of Edible bird's nest, 15 parts of Abalone, 15 parts of sea cucumber, 15 parts of shark cartilage, 15 parts of turtle rim, 20 parts of gamma globulin, 20 parts of non-transgenic soybean lecithin, 40 parts of camellia oil, 20 parts of seabuckthorn seed oil, 5 parts of *Lentinus edodes* peptides, 5 parts of amino acids, and 0.5 parts of nano zinc oxide.

5. A preparation method of the composition for adjuvant treatment of the tumor as claimed in claim 1, comprising:

step 1: adding water to the *Cordyceps sinensis*, the *Dendrobium officinale* Kimura et Migo, the red ginseng, the *Eucommia ulmoides* male flower, the *Lycium chinense*, the okra, the mulberry, and the Chinese yam to obtain a first mixture, with a water addition of 20-30 times a weight of the *Cordyceps sinensis*, decocting the first mixture for 150-200 minutes to obtain a decocted mixture, filtering the decocted mixture with an 800-mesh filter to obtain a mixed nutrient solution, putting the mixed nutrient solution into a fermentation tank, adding mucor and brown sugar into the fermentation tank for fermentation, taking out a fermented product after 80-100 days of fermentation, adding anhydrous ethanol into the fermented product with an ethanol addition of 30%-50% of a weight of the mixed nutrient solution, standing the fermented product added with the anhydrous ethanol for 12-24 hours, and filtering the stood product to obtain a filtrate for later use;

step 2: adding water to the shark fin, the Edible bird's nest, the Abalone, the sea cucumber, the shark cartilage, the turtle rim to obtain a second mixture, with a water addition of 15-25 times of a weight of the shark fin, decocting the second mixture for 40-56 hours to obtain a mixed nutritional paste, and then drying the mixed nutritional paste to obtain mixed peptides; and step 3: mixing the filtrate for later use obtained in the step 1 and the mixed peptides obtained in the step 2 with the gamma globulin, the non-transgenic soybean lecithin, the camellia oil, the seabuckthorn seed oil, the *Lentinus edodes* peptides, the amino acids, and the nano zinc oxide to obtain a third mixture, and uniformly stirring the third mixture to obtain the composition.

6. The preparation method as claimed in claim 5, wherein an addition amount of the mucor is in a range of 0.25% to 0.65% of the weight of the mixed nutrient solution.

7. The preparation method as claimed in claim 5, wherein an addition amount of the brown sugar is in a range of 5% to 8% of the weight of the mixed nutrient solution.

8. A preparation method of the composition for adjuvant treatment of the tumor as claimed in claim 2, comprising:

step 1: adding water to the *Cordyceps sinensis*, the *Dendrobium officinale* Kimura et Migo, the red ginseng, the *Eucommia ulmoides* male flower, the *Lycium chinense*, the okra, the mulberry, and the Chinese yam to obtain a first mixture, with a water addition of 20-30 times a weight of the *Cordyceps sinensis*, decocting the first mixture for 150-200 minutes to obtain a decocted mixture, filtering the decocted mixture with an 800-mesh filter to obtain a mixed nutrient solution, putting the mixed nutrient solution into a fermentation tank, adding mucor and brown sugar into the fermentation tank for fermentation, taking out a fermented product after 80-100 days of fermentation, adding anhydrous ethanol into the fermented product with an ethanol addition of 30%-50% of a weight of the mixed nutrient solution, standing the fermented product added with the anhydrous ethanol for 12-24 hours, and filtering the stood product to obtain a filtrate for later use;

step 2: adding water to the shark fin, the Edible bird's nest, the Abalone, the sea cucumber, the shark cartilage, the turtle rim to obtain a second mixture, with a water addition of 15-25 times of a weight of the shark fin, decocting the second mixture for 40-56 hours to obtain a mixed nutritional paste, and then drying the mixed nutritional paste to obtain mixed peptides; and step 3: mixing the filtrate for later use obtained in the step 1 and the mixed peptides obtained in the step 2 with the gamma globulin, the non-transgenic soybean lecithin, the camellia oil, the seabuckthorn seed oil, the *Lentinus edodes* peptides, the amino acids, and the nano zinc oxide to obtain a third mixture, and uniformly stirring the third mixture to obtain the composition.

9. The preparation method as claimed in claim 8, wherein an addition amount of the mucor is in a range of 0.25% to 0.65% of the weight of the mixed nutrient solution.

10. The preparation method as claimed in claim 8, wherein an addition amount of the brown sugar is in a range of 5% to 8% of the weight of the mixed nutrient solution.

11. A preparation method of the composition for adjuvant treatment of the tumor as claimed in claim 3, comprising:

step 1: adding water to the *Cordyceps sinensis*, the *Dendrobium officinale* Kimura et Migo, the red ginseng, the *Eucommia ulmoides* male flower, the *Lycium chinense*, the okra, the mulberry, and the Chinese yam to obtain a first mixture, with a water addition of 20-30 times a weight of the *Cordyceps sinensis*, decocting the first mixture for 150-200 minutes to obtain a decocted mixture, filtering the decocted mixture with an 800-mesh filter to obtain a mixed nutrient solution, putting the mixed nutrient solution into a fermentation tank, adding mucor and brown sugar into the fermentation tank for fermentation, taking out a fermented product after 80-100 days of fermentation, adding anhydrous ethanol into the fermented product with an ethanol addition of 30%-50% of a weight of the mixed nutrient solution, standing the fermented product added with the anhydrous ethanol for 12-24 hours, and filtering the stood product to obtain a filtrate for later use;

step 2: adding water to the shark fin, the Edible bird's nest, the Abalone, the sea cucumber, the shark cartilage, the turtle rim to obtain a second mixture, with a water addition of 15-25 times of a weight of the shark fin, decocting the second mixture for 40-56 hours to obtain a mixed nutritional paste, and then drying the mixed nutritional paste to obtain mixed peptides; and step 3: mixing the filtrate for later use obtained in the step 1 and the mixed peptides obtained in the step 2 with the gamma globulin, the non-transgenic soybean lecithin, the camellia oil, the seabuckthorn seed oil, the *Lentinus edodes* peptides, the amino acids, and the nano zinc oxide to obtain a third mixture, and uniformly stirring the third mixture to obtain the composition.

12. The preparation method as claimed in claim 11, wherein an addition amount of the mucor is in a range of 0.25% to 0.65% of the weight of the mixed nutrient solution.

13. The preparation method as claimed in claim 11, wherein an addition amount of the brown sugar is in a range of 5% to 8% of the weight of the mixed nutrient solution.

14. A preparation method of the composition for adjuvant treatment of the tumor as claimed in claim 4, comprising:

step 1: adding water to the *Cordyceps sinensis*, the *Dendrobium officinale* Kimura et Migo, the red ginseng, the *Eucommia ulmoides* male flower, the *Lycium chinense*, the okra, the mulberry, and the Chinese yam to obtain a first mixture, with a water addition of 20-30 times a weight of the *Cordyceps sinensis*, decocting the first mixture for 150-200 minutes to obtain a decocted mixture, filtering the decocted mixture with an 800-mesh filter to obtain a mixed nutrient solution, putting the mixed nutrient solution into a fermentation tank, adding mucor and brown sugar into the fermentation tank for fermentation, taking out a fermented product after 80-100 days of fermentation, adding anhydrous ethanol into the fermented product with an ethanol addition of 30%-50% of a weight of the mixed nutrient solution, standing the fermented product added with the anhydrous ethanol for 12-24 hours, and filtering the stood product to obtain a filtrate for later use;

step 2: adding water to the shark fin, the Edible bird's nest, the Abalone, the sea cucumber, the shark cartilage, the turtle rim to obtain a second mixture, with a water addition of 15-25 times of a weight of the shark fin, decocting the second mixture for 40-56 hours to obtain a mixed nutritional paste, and then drying the mixed nutritional paste to obtain mixed peptides; and step 3: mixing the filtrate for later use obtained in the step 1 and the mixed peptides obtained in the step 2 with the gamma globulin, the non-transgenic soybean lecithin, the camellia oil, the seabuckthorn seed oil, the *Lentinus edodes* peptides, the amino acids, and the nano zinc oxide to obtain a third mixture, and uniformly stirring the third mixture to obtain the composition.

15. The preparation method as claimed in claim 14, wherein an addition amount of the mucor is in a range of 0.25% to 0.65% of the weight of the mixed nutrient solution.

16. The preparation method as claimed in claim 14, wherein an addition amount of the brown sugar is in a range of 5% to 8% of the weight of the mixed nutrient solution.

17. A method for treating tumor as an adjuvant treatment comprising administering the composition of claim 1 to a patient in need thereof.

18. A method for treating tumor as an adjuvant treatment comprising administering the composition of claim 2 to a patient in need thereof.

19. A method for treating tumor as an adjuvant treatment comprising administering the composition of claim 3 to a patient in need thereof.

20. A method for treating tumor as an adjuvant treatment comprising administering the composition of claim 1 to a patient in need thereof.

* * * * *